United States Patent
Coffman

(10) Patent No.: US 10,835,426 B2
(45) Date of Patent: Nov. 17, 2020

(54) SANITARY PAD

(71) Applicant: Rebecca Coffman, Kansas City, MO (US)

(72) Inventor: Rebecca Coffman, Kansas City, MO (US)

(*) Notice: Subject to any disclaimer, the term of this patent is extended or adjusted under 35 U.S.C. 154(b) by 572 days.

(21) Appl. No.: 15/676,441

(22) Filed: Aug. 14, 2017

(65) Prior Publication Data

US 2018/0042783 A1 Feb. 15, 2018

Related U.S. Application Data

(60) Provisional application No. 62/374,301, filed on Aug. 12, 2016.

(51) Int. Cl.
| | | |
|---|---|---|
| *A61F 13/475* | (2006.01) | |
| *A61F 13/47* | (2006.01) | |
| *A61L 15/58* | (2006.01) | |
| *A61F 13/49* | (2006.01) | |
| *A61F 13/15* | (2006.01) | |

(52) U.S. Cl.
CPC ...... *A61F 13/4756* (2013.01); *A61F 13/4704* (2013.01); *A61L 15/58* (2013.01); *A61F 2013/15569* (2013.01); *A61F 2013/49076* (2013.01)

(58) Field of Classification Search
CPC .............. A61F 13/4756; A61F 13/4704; A61F 2013/15569; A61F 2013/49076; A61F 13/47218; A61L 15/58
See application file for complete search history.

(56) References Cited

U.S. PATENT DOCUMENTS

| | | | | |
|---|---|---|---|---|
| 4,624,666 A | * | 11/1986 | DeRossett | A61F 13/539 604/366 |
| 4,731,065 A | * | 3/1988 | Yamada | A61F 13/472 604/355 |
| 4,743,245 A | | 5/1988 | Lassen et al. | |
| 4,988,344 A | * | 1/1991 | Reising | A61F 13/535 604/358 |
| 5,197,959 A | * | 3/1993 | Buell | A61F 13/15203 604/358 |
| 5,795,344 A | * | 8/1998 | Chappell | A61F 13/533 604/379 |
| 6,059,763 A | | 5/2000 | Brown | |
| 6,348,047 B1 | | 2/2002 | Harper | |
| 6,939,333 B1 | | 9/2005 | Franklin | |
| 6,958,430 B1 | * | 10/2005 | Marinelli | A61F 13/474 604/365 |
| 9,066,837 B2 | * | 6/2015 | Kim | A61F 13/4756 |
| 10,292,873 B2 | * | 5/2019 | Koulai | A61F 13/47272 |
| 2004/0147895 A1 | * | 7/2004 | Mizutani | A61F 13/47209 604/385.17 |

(Continued)

OTHER PUBLICATIONS

Definition of Flange from Dictionary.com (Year: 2020).*

*Primary Examiner* — Tatyana Zalukaeva
*Assistant Examiner* — Gabriella E Burnette
(74) *Attorney, Agent, or Firm* — Boudwin Intellectual Property; Daniel Boudwin

(57) ABSTRACT

A sanitary pad. The sanitary pad includes an elongated pad having an upper surface and a lower surface. An upraised member having a first lateral side and a second lateral side is disposed on the upper surface. A plurality of channels are disposed along the first lateral side and the second lateral side.

18 Claims, 3 Drawing Sheets

(56) References Cited

U.S. PATENT DOCUMENTS

| | | | |
|---|---|---|---|
| 2007/0225671 A1* | 9/2007 | Angel, Jr. | A61F 13/4756 604/385.17 |
| 2009/0036854 A1* | 2/2009 | Guidotti | A61F 13/47218 604/369 |
| 2010/0292665 A1 | 11/2010 | Sigel et al. | |
| 2011/0060303 A1* | 3/2011 | Bissah | A61F 13/53717 604/372 |
| 2013/0231622 A1* | 9/2013 | Dieringer | A61F 13/47218 604/372 |
| 2015/0073370 A1* | 3/2015 | Noda | A61F 13/539 604/378 |
| 2015/0328063 A1* | 11/2015 | Esping Ostlin | A61F 13/533 604/379 |
| 2017/0354549 A1* | 12/2017 | Cho | A61F 13/47218 |
| 2017/0367901 A1* | 12/2017 | Ellis | A61F 13/58 |
| 2019/0314220 A1* | 10/2019 | Hardie | A61F 13/514 |

* cited by examiner

SANITARY PAD

CROSS REFERENCE TO RELATED APPLICATIONS

This application claims the benefit of U.S. Provisional Application No. 62/374,301 filed on Aug. 12, 2016. The above identified patent application is herein incorporated by reference in its entirety to provide continuity of disclosure.

BACKGROUND OF THE INVENTION

The present invention relates to sanitary pads. More specifically, the present invention provides a sanitary pad with an upraised member featuring a plurality of channels on opposing lateral sides.

Many women rely on sanitary pads to absorb menstrual flow. Traditional sanitary pads frequently fail to remain in position when worn as they are not contoured to conform to a woman's body. This leads to discomfort and leakage of menstrual flow through clothing and bedding as the sanitary pad shifts due to movement. This can result in unnecessary expenses as the clothing and bedding must be replaced or cleaned, in addition to any emotional injury or embarrassment caused by this leakage. Therefore, a sanitary pad that conforms to the user's body to prevent shifting is needed.

In light of the devices disclosed in the known art, it is submitted that the present invention substantially diverges in design elements from the known art and consequently it is clear that there is a need in the art for an improvement to existing instrument straps. In this regard, the instant invention substantially fulfills these needs.

SUMMARY OF THE INVENTION

In view of the foregoing disadvantages inherent in the known types of sanitary pads now present in the prior art, the present invention provides a sanitary pad wherein the same can be utilized for providing convenience for the user when absorbing amounts of menstrual fluid.

The present system comprises an elongated pad having an upper surface and a lower surface. An upraised member having a first lateral side and a second lateral side is disposed on the upper surface. A plurality of channels are disposed along the first lateral side and the second lateral side. In some embodiments, the lower surface comprises an adhesive. In another embodiment, a cover is removably secured to the lower surface, wherein the cover is configured to protect the adhesive until used. In other embodiments, a front flange extends along the length of the upper surface from a front side of the upraised member. In yet another embodiment, the front flange slopes downwards from the front side to the upper surface. In some embodiments, a rear flange extends along the length of the upper surface from a rear side of the upraised member. In another embodiment, the rear flange slopes downwards from the rear side to the upper surface. In other embodiments, a trench disposed along an outer edge of the elongated pad. In yet another embodiment, the upraised member further comprises a depression disposed at an upper side thereof. In some embodiments, the elongated pad comprises an absorbent material. In another embodiment, the elongated pad comprises a flexible material. In other embodiments, the upraised member is disposed centrally on the upper side.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
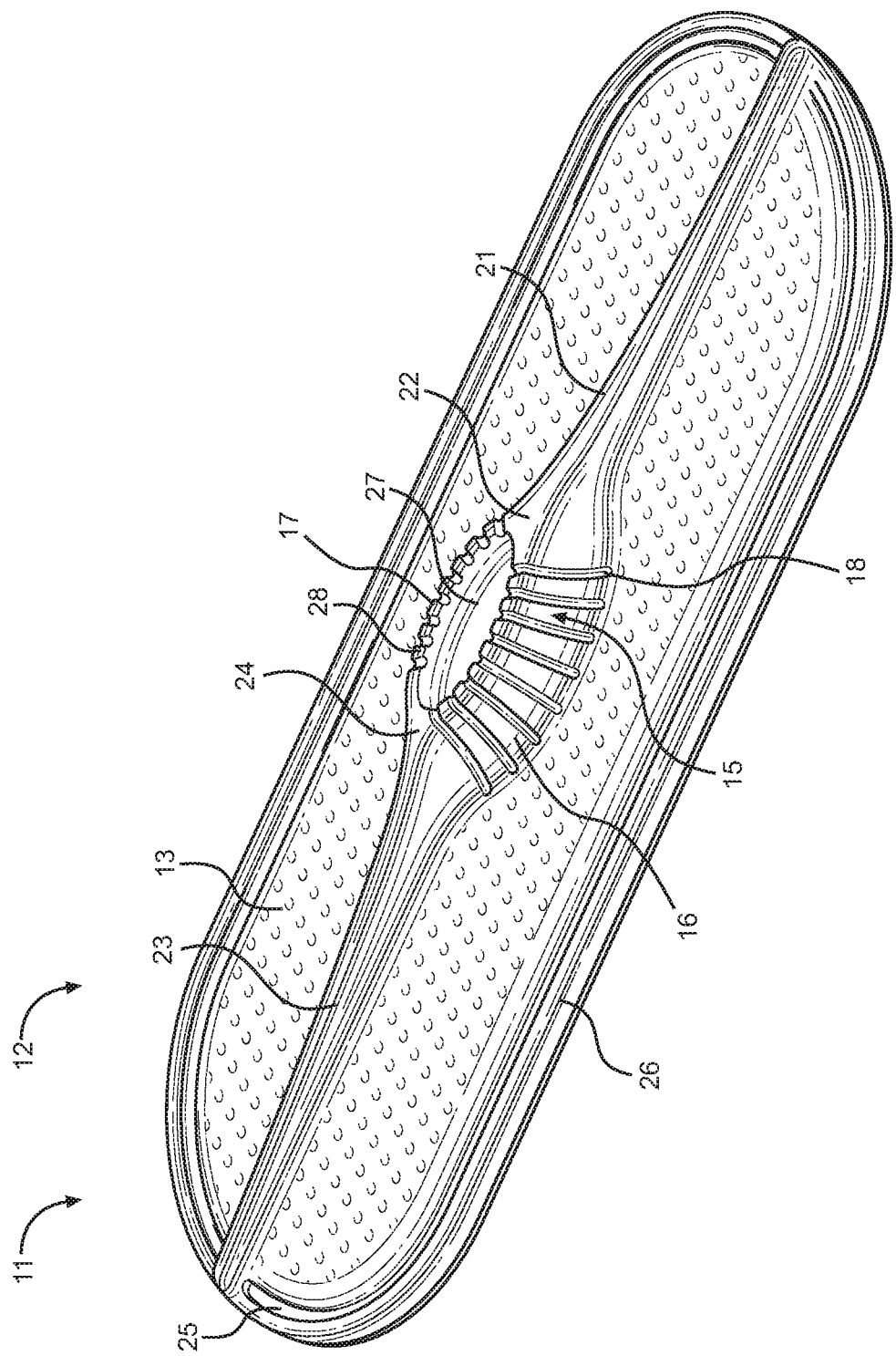
FIG. 1 shows a perspective view of an embodiment of the sanitary pad.

Reference is made herein to the attached drawings. Like reference numerals are used throughout the drawings to depict like or similar elements of the sanitary pad. The figures are intended for representative purposes only and should not be considered to be limiting in any respect.

Referring now to FIG. 1, there is shown a perspective view of an embodiment of the sanitary pad. The sanitary pad 11 comprises an elongated pad 12 having an upper surface 13 and a lower surface. The elongated pad 12 comprises an absorbent and flexible material such that the elongated pad 12 can absorb menstrual fluid and conform to a user. In the illustrated embodiment, the elongated pad 12 comprises a rectangular cross-section, wherein the rectangle includes rounded corners, however, in alternate embodiments, the elongated pad 12 comprises other cross-sections, such as, but not limited to, ovoid and rectangular having a bowed central portion.

The elongated pad 12 further comprises an upraised member 15 disposed on the upper surface 13. In the illustrated embodiment, the upraised member 15 is disposed in a center of the upper surface 13 and comprises a front side 22, a rear side 24, a first lateral side wall (hereafter referred to as first lateral side) 16 and a second lateral side wall (hereafter referred to as second lateral side) 17. The upraised member 15 is configured to rest flush against the genitalia of a user. In this way, the upraised member 15 allows a user to minimize the distance between the user and the sanitary pad 11, such that any menstrual flow is immediately introduced to the sanitary pad 11. The upraised member 15 comprises an absorbent material and is configured to wick away any flow to the elongated pad 12. In some embodiments, the upraised member 15 further comprises a coating disposed along the upraised member 15 where the upraised member 15 contacts the user, wherein the coating is configured to prevent chafing in the user. A depression 27 is disposed on an upper side 28 of the upraised member 15. The depression 27 extends partially into the upraised member 15 towards the upper surface 13 such that the depression 27 is configured to receive a volume of menstrual fluid therein. In the illustrated embodiment, the depth of the depression 27 is one third of the height of the upraised member 15. In this way, the depression 27 allows periods of increased flow to be contained therein until the fluid is absorbed into the material of the sanitary pad 11. The depression 27 is unitary with the upper surface 13, such that the fluid disposed within the depression 27 is wicked into and along the sanitary pad 11. A plurality of channels 18 are disposed on the first and second lateral sides 16, 17 and are configured to guide fluid from the depression 27 to the upper surface 13 in the event that the fluid volume exceeds the volume of the depression 27. This allows the fluid to be dispersed across the surface area of the upper surface 13 to be more quickly absorbed.

The sanitary pad 11 further comprises a front flange 21 extending from the front side 22 that is configured to contour and engage gently with the anatomy of a user. In the illustrated embodiment, the front flange 21 slopes downward from the upper side 28 to meet the upper surface 13. In alternate embodiments, the front flange 21 extends from a point on the front side 22 between the upper side 28 and the upper surface 13 to minimize the invasiveness of the front flange 21 and provide increased comfort for the user. A rear flange 23 extends from the rear side 24 and is configured to contour and engage gently with the buttocks of a user. In the illustrated embodiment, the rear flange 24 slopes downwards from the upper side 28 to meet the upper surface 13. In this way, the front and rear flanges 21, 23 engage with a user to prevent the sanitary pad 11 from moving during use. In the illustrated embodiment, the front and rear flanges 21, 23 taper from both the upraised member 15 towards opposing ends of the elongated pad 12 and from the upper surface 13 to an upper end of the front and rear flanges 21, 23. This allows the upraised member 15 to maintain contact with the user at all times to further minimize the risk of leakage. In some embodiments, the front and rear flanges 21, 23 further comprise a coating configured to prevent chafing in the user at the points the front and rear flanges 21, 23 contact the user.

In the illustrated embodiment, the sanitary pad 11 further comprises a trench 25 extending along an outer edge 26 of the elongated pad 12. The trench 25 is configured to receive fluid therein. Should the flowrate of fluid exceed the absorbency of the sanitary pad 11, excess fluid is first collected within the trench 25, containing the fluid until it can be absorbed. In this way, the trench 25 provides an additional layer of protection against leaks. In the illustrated embodiment, the front and rear flanges 21, 23 extend through the trench 25.

Figure 2:
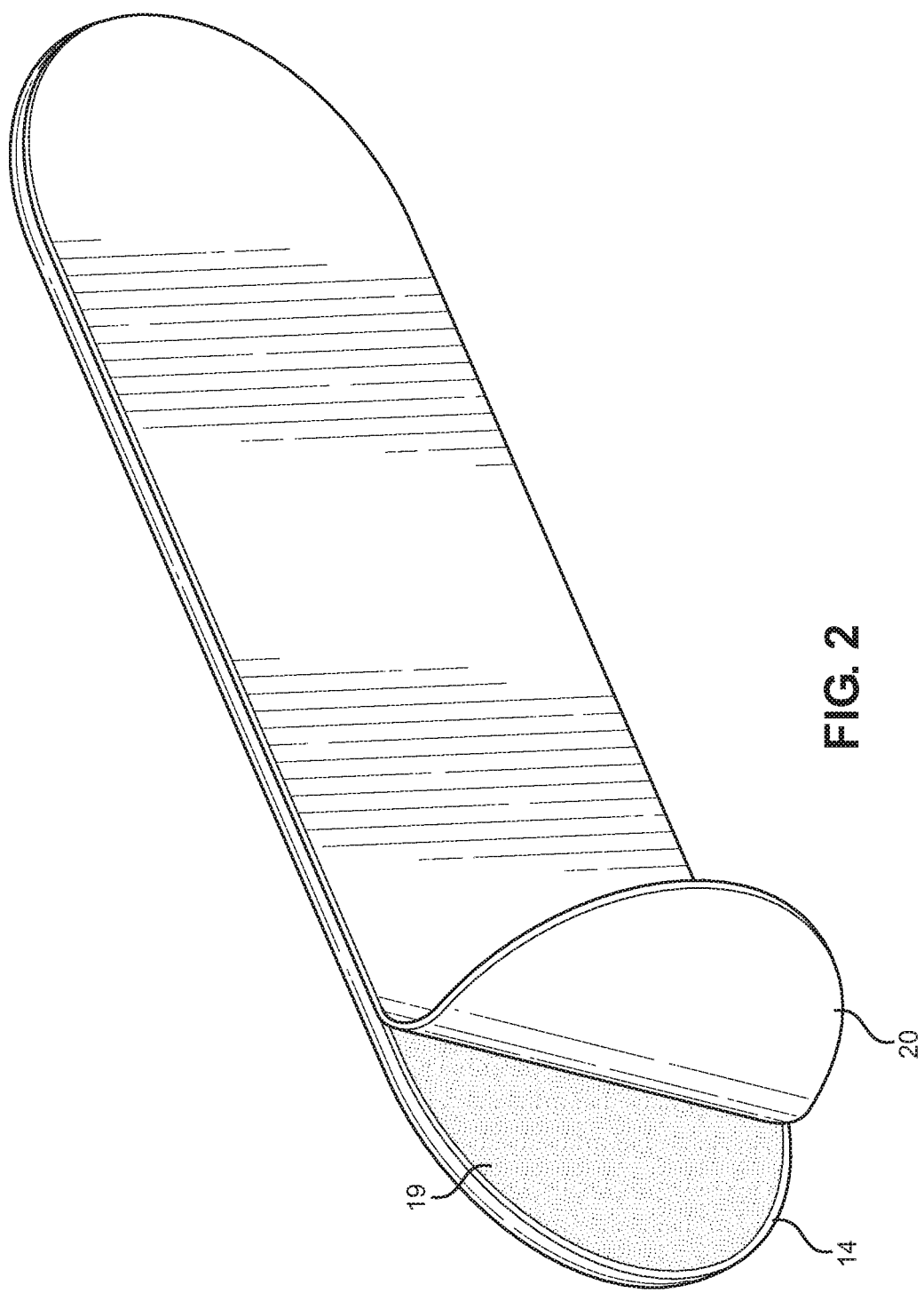
FIG. 2 shows a lower view of an embodiment of the sanitary pad.

Referring now to FIG. 2, there is shown a lower view of an embodiment of the sanitary pad. In the illustrated embodiment, the sanitary pad further comprises an adhesive 19 disposed across the lower surface 14 of the elongated pad. The adhesive 19 is configured to removably secure the sanitary pad to a surface, such as an inner surface of an undergarment. In this way, the adhesive 19 provides increased stability to the sanitary pad, preventing the sanitary pad from moving from a desired location. The adhesive 19 is protected by a cover 20 that is removably secured thereto. The cover 20 is configured to maintain the viability of the adhesive 19 until the user determines to use the sanitary pad.

Figure 3:
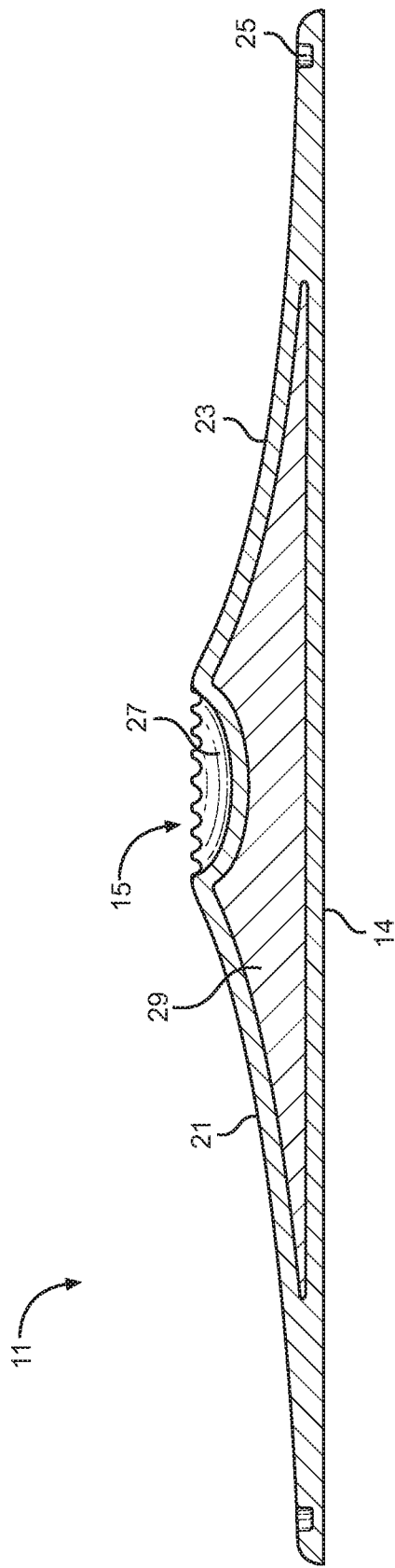
FIG. 3 shows a cross-sectional view of an embodiment of the sanitary pad.

Referring now to FIG. 3, there is shown a cross-sectional view of an embodiment of the sanitary pad. In the illustrated embodiment, the sanitary pad 11 comprises an outer shell of an absorbent and comfortable material, such as, but not limited to, cotton. This provides the user with increased comfort with all external areas the user is in contact with. These external surfaces are configured to wick moisture and fluid towards an interior volume 29 of the sanitary pad 11, wherein the interior volume 29 contains an absorbent material therein. The absorbent material is configured to have a greater absorbency than the external materials, such as those of the upraised member 15 and the front and rear flanges 21, 23. The depression 27 and the trench 25 serve as containment zones, allowing the accumulation of fluid therein, such that the large volume of fluid is wicked into the interior volume 29 over time.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A sanitary pad, comprising: an elongated pad having an upper surface and a lower surface; an upraised member having a first lateral side wall and a second lateral side wall disposed on the upper surface; wherein a plurality of channels is formed within the first lateral side wall and the second lateral side wall; and wherein the plurality of channels extends between an upper edge of the upraised member and the upper surface of the elongated pad.

2. The sanitary pad of claim 1, wherein the lower surface comprises an adhesive.

3. The sanitary pad of claim 2, further comprising a cover removably secured to the lower surface, wherein the cover is configured to protect the adhesive.

4. The sanitary pad of claim 1, further comprising a front ridge extending along the length of the upper surface from a front side of the upraised member.

5. The sanitary pad of claim 4, wherein the front ridge slopes downwards from the front side to the upper surface.

6. The sanitary pad of claim 1, further comprising a rear ridge extending along the length of the upper surface from a rear side of the upraised member.

7. The sanitary pad of claim 6, wherein the rear ridge slopes downwards from the rear side to the upper surface.

8. The sanitary pad of claim 1, further comprising a trench disposed along an outer edge of the elongated pad.

9. The sanitary pad of claim 1, wherein the upraised member further comprises a depression disposed at an upper side thereof.

10. The sanitary pad of claim 1, wherein the elongated pad comprises an interior volume having an absorbent material therein.

11. The sanitary pad of claim 1, wherein the elongated pad is flexible.

12. The sanitary pad of claim 1, wherein the upraised member is disposed centrally on the upper side.

13. The sanitary pad of claim 4, wherein the front ridge is disposed centrally along the upper surface extending between the front side of the upraised member and a front end of the elongated pad.

14. The sanitary pad of claim 6, wherein the rear ridge is disposed centrally along the upper surface extending between the rear side of the upraised member and a rear end of the elongated pad.

15. The sanitary pad of claim 4, wherein the front ridge extends through a trench defined within the upper surface about an outer edge of the elongated pad.

16. The sanitary pad of claim 6, wherein the rear ridge extends through a trench defined within the upper surface about an outer edge of the elongated pad.

17. A method of using a sanitary pad as disclosed in claim 1, comprising:
- providing an elongated pad having an upraised member extending from an upper surface thereof;
- wherein the upraised member comprises a plurality of channels in each of a first lateral side and a second lateral side thereof;
- placing the elongated pad such that the upraised member rests flush against genitalia of a user, such that menstrual flow therefrom is immediately introduced to the elongated pad.

18. The method of claim 17, further comprising engaging a rear ridge extending from a rear side of the upraised member between each buttock of the user.

* * * * *